United States Patent [19]

Clavin

[11] Patent Number: 4,653,483
[45] Date of Patent: Mar. 31, 1987

[54] COSMETIC TAPE, APPLICATOR THEREFOR AND METHOD

[76] Inventor: Harold D. Clavin, 2001 Santa Monica Blvd., Santa Monica, Calif. 90404

[21] Appl. No.: 681,857
[22] PCT Filed: Oct. 26, 1983
[86] PCT No.: PCT/US83/01663
   § 371 Date: Jul. 5, 1984
   § 102(e) Date: Jul. 5, 1984
[87] PCT Pub. No.: WO84/01891
   PCT Pub. Date: May 24, 1984

Related U.S. Application Data

[63] Continuation-in-part of Ser. No. 440,846, Nov. 12, 1982, Pat. No. 4,432,347.

[51] Int. Cl.$^4$ .............................................. A61H 5/00
[52] U.S. Cl. ................................. 128/76.5; 128/1 R; 128/20; 128/163; 128/156; 132/53; 132/88.5
[58] Field of Search ............... 128/1 R, 155, 156, 163, 128/159, 20, 132 R, 171, 355, 76 B, 76.5, 76, 153; 132/88.7, 88.5, 53, 1 R, DIG. 3; 604/294, 307, 893; 427/208; 2/12, 15

[56] References Cited

U.S. PATENT DOCUMENTS

| D. 119,329 | 3/1940 | Leyne | 132/88.5 |
|---|---|---|---|
| 497,052 | 5/1893 | Lamb | 128/76.5 |
| 2,001,589 | 5/1935 | Steiner | 132/53 |
| 2,001,862 | 5/1935 | Battey | 128/163 |
| 2,079,256 | 5/1937 | Kaiser | 132/53 |
| 2,572,638 | 10/1951 | Loos | 128/163 |
| 2,599,359 | 6/1952 | Banks et al. | 427/208 |
| 2,695,622 | 11/1954 | Herod et al. | 128/163 |
| 2,835,259 | 5/1958 | Goodman | 132/53 |
| 2,842,142 | 7/1958 | Peck | 132/88.5 |
| 2,862,509 | 12/1958 | Porte | 132/53 |
| 2,896,613 | 7/1959 | Brown | 128/76 R |
| 2,901,100 | 8/1959 | Mueller et al. | 132/88.7 |
| 2,969,057 | 1/1961 | Simmons | 128/155 |
| 3,068,863 | 12/1962 | Bowman | 128/163 |
| 3,092,103 | 6/1963 | Mower | 128/163 |
| 3,266,500 | 8/1966 | Weld | 132/88.7 |
| 3,485,251 | 12/1969 | Brunet | 132/88.5 |
| 3,568,684 | 3/1971 | Reece | 132/1 R |
| 3,619,815 | 11/1971 | Towner, Jr. | 128/132 R |
| 3,776,240 | 12/1973 | Woodson | 128/20 |
| 3,789,856 | 2/1974 | Bomba | 132/88.5 |
| 3,884,232 | 5/1975 | Braun | 132/88.7 |
| 3,935,872 | 2/1976 | Ayloit | 132/88.7 |
| 3,991,754 | 11/1976 | Gertzman | 128/156 |
| 3,995,635 | 12/1976 | Higuchi et al. | 604/294 |
| 4,022,204 | 5/1977 | Le Boeuf et al. | 128/155 |
| 4,024,879 | 5/1977 | Stryker | 132/88.5 |
| 4,033,364 | 7/1977 | Inzana et al. | 132/88.5 |
| 4,134,401 | 1/1979 | Galician | 128/163 |
| 4,202,925 | 5/1980 | Dabroski | 128/156 |
| 4,432,347 | 2/1984 | Clavin | 128/20 |

FOREIGN PATENT DOCUMENTS

| 431950 | 7/1926 | Fed. Rep. of Germany | 128/76.5 |
|---|---|---|---|
| 2012161 | 9/1971 | Fed. Rep. of Germany | 132/88.5 |
| 2512651 | 3/1983 | France | 132/1 R |
| 43543 | 3/1908 | Switzerland | 128/76.5 |
| 1529143 | 10/1978 | United Kingdom | 604/294 |
| 491378 | 11/1975 | U.S.S.R. | 128/1 R |
| 519194 | 8/1976 | U.S.S.R. | 128/1 R |
| 556804 | 6/1977 | U.S.S.R. | 128/1 R |
| 611613 | 6/1978 | U.S.S.R. | 128/1 R |
| 648222 | 2/1979 | U.S.S.R. | 128/1 R |
| 718104 | 2/1980 | U.S.S.R. | 128/1 R |

Primary Examiner—Gene Mancene
Assistant Examiner—J. R. Hakomaki
Attorney, Agent, or Firm—Pons, Smith, Lande & Rose

[57] ABSTRACT

An adhesive tape and method for use thereof in non-surgically taking a tuck in loose skin such as that comprising the upper eyelid. When applied to a drooping upper eyelid by stretching the skin of the eyelid away from ciliary margin, applying a precut, preshaped tape to the eyelid, and then folding the skin of the upper eyelid down to be attached to the other side of the tape and then back upon itself, a pseudo upper blepharoplasty is effected, which can be left in place for extended periods of time, thus avoiding surgery. The adhesive strip has a backing and adhesive such as to make the strip very thin, very soft and pliable, strong, tear resistant, easily conformed to body contours, non-irritating and water resistant. An applicator device having a receiving surface for releasably holding the adhesive strip to facilitate the applying of the strip to the skin surface.

6 Claims, 18 Drawing Figures

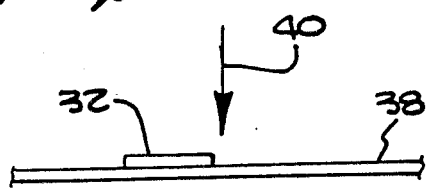
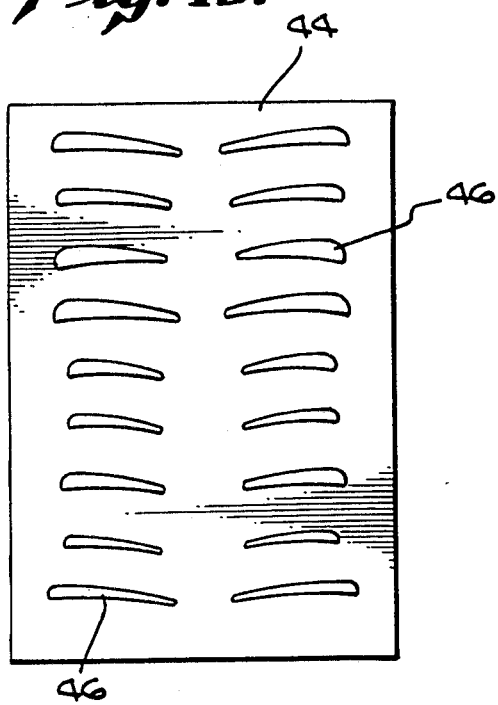
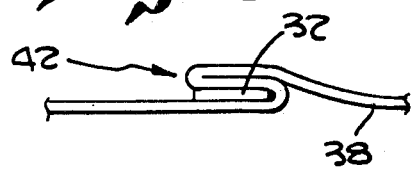
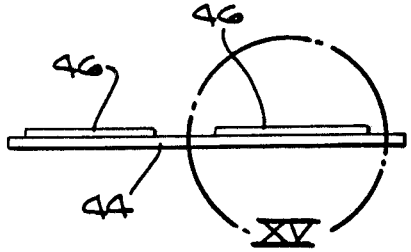
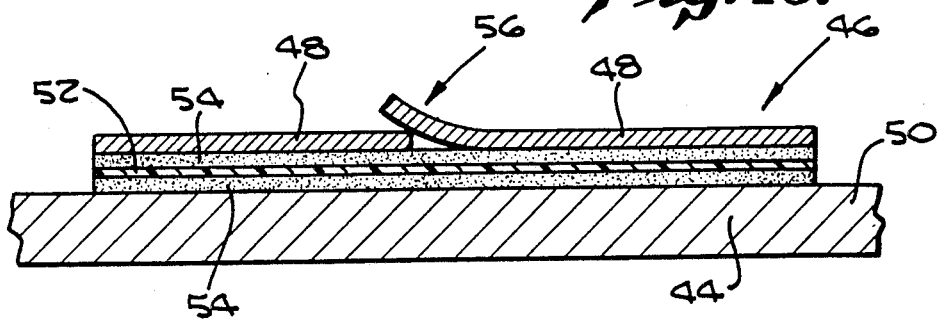

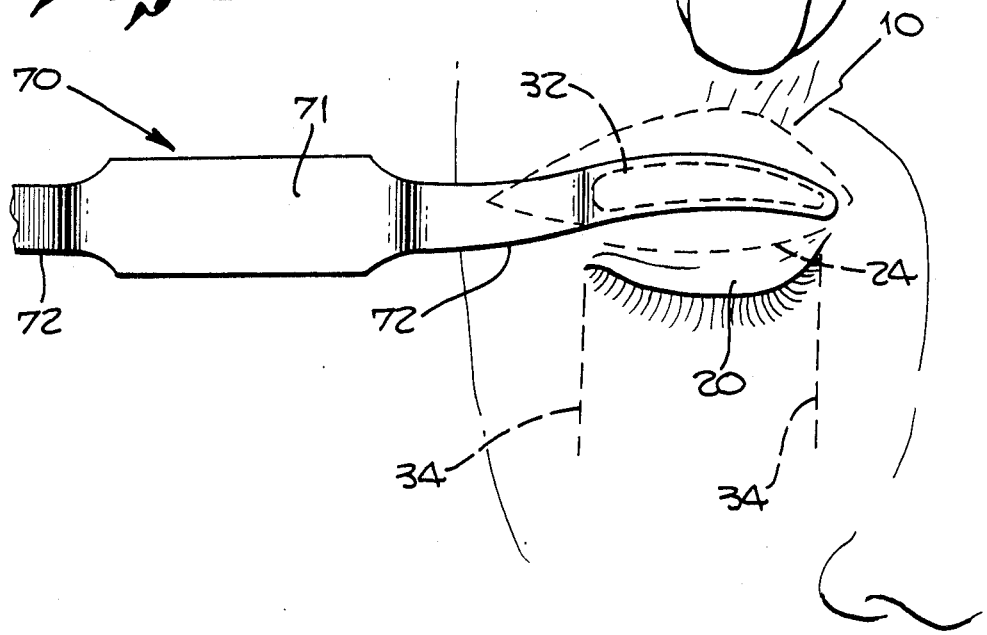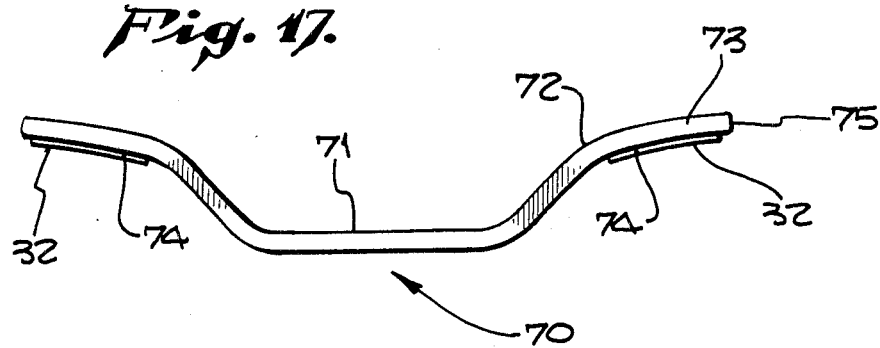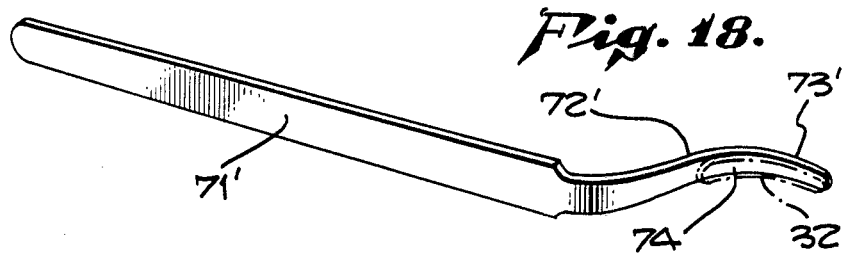

COSMETIC TAPE, APPLICATOR THEREFOR AND METHOD

This application is a continuation-in-part of parent application Ser. No. 440,846 filed Nov. 12, 1982 now U.S. Pat. No. 4,432,347 on a Cosmetic Tape and Method.

BACKGROUND OF THE INVENTION

The present invention relates to precut, preshaped adhesive tape strips or members for application to an upper eyelid to retain a fold in the skin thereof, an applicator device for facilitating placement of such an adhesive member on the skin surface of the eyelid, and a method for use of the tape strip in nonsurgically taking a tuck in loose skin, such as at the upper eyelid.

A cutaway drawing through the upper eyelid is shown in FIG. 1. The upper eyelid, generally indicated as 10, moves down over the eyeball 12 when the eyes are closed, and retracts over the cornea 14 to expose the iris 16 and pupilary opening 18 when the eye is open. The skin of the upper eyelid 10 along the ciliary margin 20 is held relatively rigid by a thin strip of cartilage known as the tarsal plate 22. The skin above the ciliary margin 20 is thin and supple and tends to fold at what is referred to as the supra tarsal fold 24.

Particularly as part of the natural aging process, the skin of the upper eyelid can sag or droop into positions such as those shown ghosted and labelled 26 in FIG. 1. The result is a bagging or festooning of the upper eyelid as shown in FIG. 2. A similar condition occurs naturally in the eyes of many persons of Oriental extraction due to a difference in eye physiology.

When the natural or developed droop reaches the lower ghosted position 26 of FIG. 1 adjacent the eyelashes 28, several things can happen. First, the actual vision above the horizontal can be affected. That is, merely rotating the eyeball 12 in an upward direction does not provide a view in that direction since the line of vision is covered by the drooped portion 26 of the eyelid 10. Even without the reduced vision, the natural puffiness and droop in the non-Oriental eye tends to make the associated eye (and, therefore, the person) look older. Additionally, in women, it can interfere with the application of eye makeup.

Statistically, there are at least 44 million women over the age of 40 in the United States alone. It can be assumed that a drooping condition such as that shown in FIG. 2 is of some bother to at least a substantial portion of them. The condition can be corrected surgically in the manner shown in FIGS. 3 and 4. And, in fact, several hundred thousand people a year have the procedure shown therein performed to alleviate the condition. As shown in FIG. 3, a strip 30 of the upper eyelid 10 is surgically removed along with some of the fat beneath the strip 30. The sides of the wound are then sutured together as shown in FIG. 4, thus removing a portion of the excess skin above the upper eyelid 10 thereby removing the droop shown in FIG. 2. Such a procedure is referred to as an upper blepharoplasty.

The above-described procedure is neither inconsequential nor inexpensive. For most of the persons afflicted with drooping eyes such as that shown in FIG. 2, the condition remains one of annoyance either due to lack of funds for the surgery or a lack of desire or willingness to have the surgery itself.

Wherefore, it is the object of the present invention to provide a tape strip member and applicator device therefor and method for providing a non-surgical temporary pseudo upper blepharoplasty.

An object of the invention is to provide an adhesive strip member for effecting a temporary pseudo upper blepharoplasty and an applicator device facilitating the placement of such an adhesive tape member on an eyelid.

Another object of the invention is to provide a method of applying an adhesive strip member to an eyelid for non-surgically taking a tuck in the loose skin of the eyelid.

Another object of the invention is to provide an adhesive strip member including a thin pliable transparent backing material and adhesive carried on opposite side surfaces of said backing material, said backing material and adhesive being cut and shaped to a predetermined configuration to be compatible with the three dimensional skin surface configuration of an eyelid and folds of skin to be formed therein.

Another object of the present invention is to provide an applicator device for facilitating the placement of such an adhesive strip member on the skin surfaces of an eyelid, said applicator device including a handle portion of generally stiff material and an applicator portion laterally offset from the handle portion, the applicator portion having a release material on a strip receiving surface thereon for cooperation with the adhesive on the adhesive strip member.

SUMMARY

The foregoing objective of effecting a temporary blepharoplasty has been accomplished by the method of the invention described and claimed in said application, U.S. Ser. No. 440,846, filed Nov. 12, 1982. The steps of the method include stretching the skin of the upper eyelid upward away from the ciliary margin thereby unfolding the natural super tarsal fold. While the skin is stretched, attaching one side of a narrow, curved, adhesive strip member of this invention having adhesive on both sides to the skin of the upper eyelid and extending substantially between the medial and lateral canthi with its bottom edge spaced above the ciliary margin about 8–12 mm and/or with its top edge above the inner fold line of the natural super tarsal fold. The tape strip member has a backing of hypo-allergenic material and adhesive such as to make the strip very thin, very soft and pliable, strong, tear resistant, easily conformed to body contours, non-irritating, and water resistant. The skin of the upper eyelid is folded down over the adhesive strip and attached to the exposed adhesive on the other side of the adhesive strip; and, the folded skin of the upper eyelid folded back upon itself with its edge along the bottom edge of the adhesive strip to form an artificial super tarsal fold which is deeper and higher than the natural fold. The application of the tape strip is facilitated by the use of an applicator device which releasably carries the tape strip to the eyelid.

DESCRIPTION OF THE DRAWINGS

FIGS. 10-12 are simplified drawings through a segment of loose skin showing the general technique and method of the present invention for producing a non-surgical tuck in the skin.

FIG. 13 is a plan view of the adhesive strips of the present invention in their preferred embodiment.

FIG. 14 is an end view of FIG. 13.

FIG. 15 is an enlarged cutaway view of FIG. 14 in the area designated.

FIG. 16 is a view similar to FIG. 7 and illustrates the use of an applicator device embodying this invention in positioning the tape strip member on the surface of the right eyelid.

FIG. 17 is an elevational view of the applicator device shown in FIG. 16.

FIG. 18 is a perspective view of a modification of the applicator device as shown in FIGS. 16 and 17.

DESCRIPTION OF THE PREFERRED EMBODIMENT

The description which follows hereinafter is with respect to the method, apparatus and applicator device of the present invention as applied to providing a temporary psuedo upper blepharoplasty. It should be recognized that the technique and materials shown can also be used for any application where it is desired to take a non-surgical tuck in loose skin. Thus, it is envisioned that the technique and materials discussed herein can be used, for example, by plastic and reconstructive surgeons for demonstrating to potential patients an approximation of the effect which will be obtained by surgery as well as by theatre makeup artists and the like in producing desired temporary visual effects.

Figure 1:
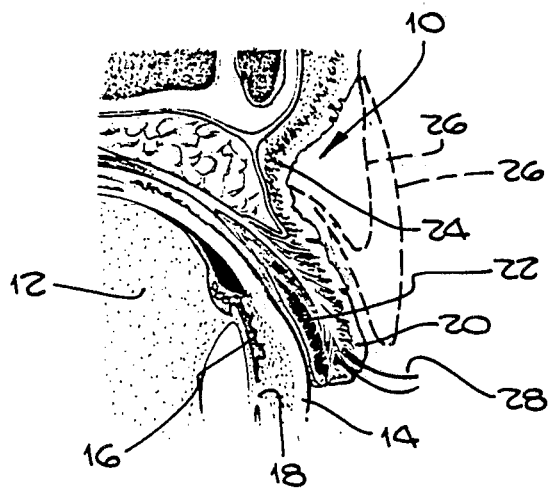
FIG. 1 is a detailed cutaway drawing of a side view of an upper eyelid.
Figure 2:
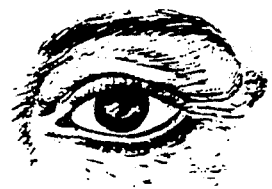
FIG. 2 is a front view of a left eye having a bagged or festooned upper eyelid.
Figure 3:
FIGS. 3 and 4 show the steps of the prior art surgical technique of blepharoplasty used to correct the condition of FIG. 2.
Figure 4:
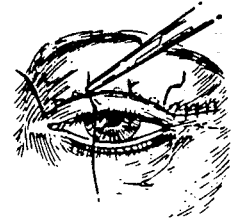
Figure 5:
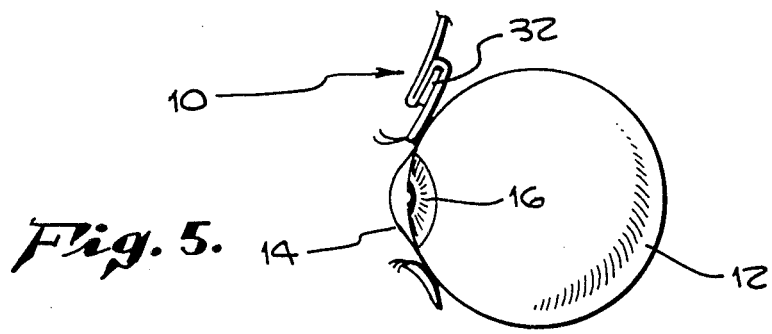
FIG. 5 is a simplified drawing of a side view through an eyeball and the eyelids showing the non-surgical technique of the present invention for forming a temporary pseudo upper blepharoplasty.

Turning first to FIG. 5, a simplified drawing through the upper eyelid 10 in conjunction with an eyeball 12 is shown, depicting the desired objective of the present invention; that is, if the natural super tarsal fold in the upper eyelid 10 is replaced by a deeper artificial super tarsal fold, an effective tuck will be taken in the loose skin of the upper eyelid 10. According to the present invention, a very thin strip of double-sided adhesive tape 32 generally less than 1 cm in width and 4 cm in length is attached to the upper eyelid 10 with the bottom edge spaced about 8-12 mm above the ciliary margin 20 and/or the top edge above the fold line of the natural super tarsal fold. The skin above the adhesive strip 32 is then folded down and then back upon itself as shown in FIG. 5 with the bottom edge of the skin aligned along the bottom edge of the tape strip 32. The adhesive strip 32 maintains the deeper and higher artificial super tarsal fold thus formed in the desired position.

Figure 6:
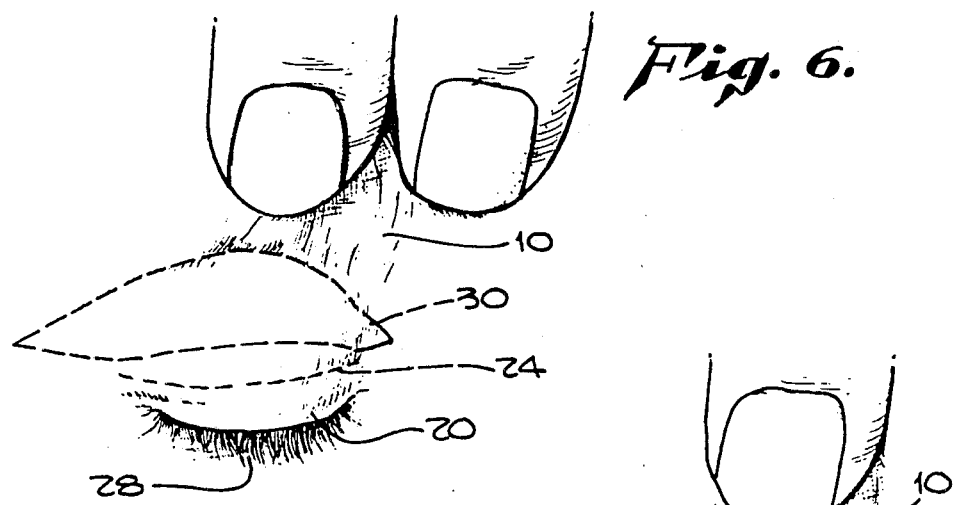
FIGS. 6-8 show the steps of performing the method of present invention on a right eye to accomplish the result of FIG. 5.
Figure 7:
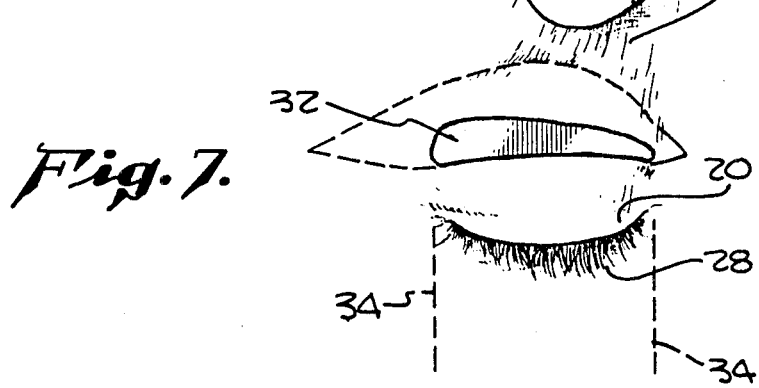
Figure 8:
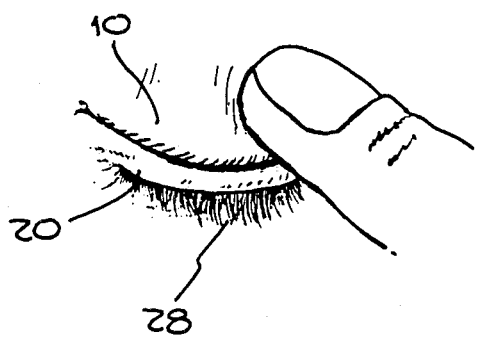

Turning now to FIGS. 6 through 8, the technique is shown in greater detail. In FIG. 6, with the eye closed, the skin of the upper eyelid 10 is stretched away from the ciliary margin 20 thus unfolding the natural super tarsal fold, which is indicated by the dashed line labelled 24. The area which would normally be removed in an actual surgical blepharoplasty is indicated by the dotted line 30 for reference. For purposed of understanding, the eye shown in FIGS. 6-8 is a right eye such that the medial canthus is to the viewer's right and the lateral canthus is to the viewer's left. With the skin stretched as in FIG. 6, a curved double-sided adhesive strip 32 is attached on its one side to the skin on the upper eyelid 10 as shown in FIG. 7. From repeated test applications, it has been determined that the sizing and configuration shown in FIG. 7 produces a desired result for a specific individual. The strip 32 can be positioned easily in either, or both, of two ways; with the bottom edge spaced from the ciliary margin 20 a given distance such as, for example, 8 to 12 mm and/or with the top edge of the strip 32 above the natural supra tarsal fold line 24. The adhesive strip 32 in its preferred embodiment is curved along the natural line of the ciliary margin 20 when the eye is opened. It is sized in length to fit between the two canthi as indicated by the two vertical dotted lines 34. In the average eye this distance is approximately 33 millimeters, such that a length for the adhesive strip 32 in that approximate amount is preferable. A maximum width of the strip 32 of less than one centimeter and approximately 5 millimeters has been found to give preferable results with a slight tapering towards the medial canthis.

Figure 9:
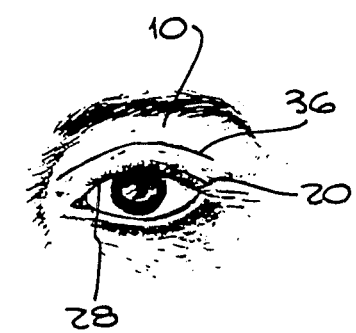
FIG. 9 is a drawing showing a left eye following the procedures of FIGS. 6-8.

With the adhesive strip 32 in place, the skin of the upper eyelid 10 is pulled gently down over the adhesive strip 32 and evenly attached thereto aligned with the bottom edge, after which it is folded back upon itself. This is shown in FIG. 8. This results in a thin tuck line at 36 which is raised and evenly spaced from the ciliary margin 20. As can be seen in FIG. 9, the result is an eye with reduced bagging of the upper eyelid 10 and with a uniform distance between the tuck line 36 and the ciliary margin 20. The artificial super tarsal fold thus created is deeper and higher and takes up a portion of the undesired skin of the upper eyelid 10. It has been found that after a period of wearing the adhesive strip 32 as thus positioned, once it is removed, the artificial super tarsal fold remains for a period of time without the necessity of the adhesive strip 32.

The general technique of the present invention with respect to taking a non-surgical tuck in any loose skin is shown in simplified form in FIGS. 10-12. Assume that it is desired to take a tuck in the skin 38 along a line as indicated by the arrow 40. The tuckline 40 can be straight curved, as desired. A double-sided adhesive strip 32 or a type to be described in greater detail hereinafter is attached along one of its adhesive surfaces to the skin 38 adjacent the intended tuck line 40. The skin on the other side of the tuck line 40, generally indicated as 42, is folded over the adhesive strip 32 to adhere to the exposed adhesive surface thereof. Fold skin 42 is then folded back upon itself as shown in FIG. 12 to create the desired tuck in the skin.

The adhesive strip of the present invention in its preferred embodiment will now be discussed in greater detail. Turning to FIGS. 13 and 14, the preferred embodiment of the present invention for use in practicing the method of pseudo blepharoplasty is shown. A release surfaced liner sheet 44 has a plurality of preformed adhesive strips 46 including a peel-off liner 48 attached thereto. The construction of each strip 46 is shown in greater detail at FIG. 15. The liner sheet 44 is preferably of a heavier paper or cardboard with a suitable surface at 50 to allow the pre-formed strips 46 to be easily removed therefrom without reducing their adhesive qualities. Each pre-formed strip 46 comprises an extremely thin backing 52 having adhesive 54 attached to either side thereof, and with a split, peel-off liner 48 on the outer surface. The peel-off liner 48 is preferably of a type which is split in the middle with an overlap as at 56. This allows the liner 48 to be easily removed from the outer adhesive 54 when the strip 46 is attached to the skin of the upper eyelid 10 by the opposite adhesive surface. To properly achieve the objects of the present invention, the backing 52 and adhesive 54 must be chosen such as to make the strip very thin, very soft and pliable, strong, tear resistant, easily conformed to body contours, non-irritating, and water resistant.

In further detail it should be noted that an exemplary strip 32 may comprise a backing material of transparent film or of film dyed to a suitable skin tone for cosmetic purposes. Such backing material may have a thickness of 1.5 mils. and in some instances the thickness may include film from 1 to 3 mils. One example of a suitable backing material is that made by Shur Medical Co., and is a breathable medical tape having substantially uniform strength in all directions. The backing is composed of randomly oriented nylon filaments fused at crossover points and is laminated on both sides with a porous layer of pressure sensitive acrylate adhesive which is permeable to air and moisture and provides good adhesive strength. The strip so formed is skin conformable, resists curling and eliminates inadvertent tape dislodgements from the skin surface. The backing material and the adhesive is hypoallergenic with no irritation potential to the skin surface. Such a backing material and adhesive substance permits moisture to pass through the interstices of the backing material which reduces moisture on the skin surface beneath the strip which is antithetical to bacterial growth. Such a porous strip member provides a strip member which may be left in position for a relatively long period of time, such as, from one to several days.

Another example of a strip member 32 suitable for use in the present invention is that made by the Minnesota Mining & Manufacturing Co. (3M) of St. Paul, Minn. under specification No. 1512-3 of August, 1981. In such a 3M tape, the strip material may comprise a backing material of transparent polyethylene film having a thickness of 1.5 mils. The adhesive coating or lamina on each side surface of the backing material may be a hypoallergenic, synthetic, acrylate based pressure sensitive adhesive. The thickness of the backing material and the adhesive lamina on opposite side surfaces thereof may result in a thickness of about 3 mils. The backing material of polyethylene film in the 3M example is generally occlusive and is suitable for use for relatively short periods of time.

Liner sheet 44 may be a skin bleached two-sided silicone treated polyethylene coated paper of a suitable basis weight.

Examples of strip members 32 as described above comprising a backing material and adhesive lamina may be cut into a shape to provide an elongated strip of varying width with curved or arcuate longitudinal edges to readily conform to the three dimensional contours or shape of the skin forming the upper eyelid. The ends of the elongated strip member 32 are blunted to prevent any sharpness which might cause discomfort when the strip member 32 is in position on an eyelid. The wider portion of the strip member is placed adjacent the lateral canthi where the loose excess skin is greater.

While in many instances the adhesive laminae applied to both faces of the backing material may be the same and have the same adhesion properties, in other instances, the adhesion strength on one side of the backing material may be greater than on the other side to facilitate retention of the tarsal fold.

While the strip member 32 provides cosmetic treatment of the eyelids, the use of strip member 32 is not limited to cosmetic purposes. It has been found that application of the strip member 32 to the upper eyelid tends to relieve the feeling of tired eyes and also improves the field of view of the eye. The feeling of tired eyes is usually accompanied by a drooping or sagging of the upper eyelid. Application of strip member 32 under such tired eye conditions and particularly when driving at night tends to stimulate a feeling of alertness and relief from the tired eye feeling.

Practice of the method of this invention, namely, attaching one side of an adhesive strip member having adhesive on both sides along one surface of the intended tuck area, folding the skin of the intended tuck area over the adhesive strip and attaching it to the exposed adhesive on the other side of the adhesive strip is facilitated by the use of an applicator device as shown in FIGS. 16, 17 and 18. FIG. 16 is similar to FIG. 7 in the illustration of the pulling back of the loose upper eyelid skin 10 by a finger and positioning of strip member 32 on the eyelid skin surface substantially as shown in FIG. 7. In FIG. 16, the strip member 32 is shown as being applied by an applicator device 70.

Applicator device 70 (FIGS. 16, 17) comprises an elongated member having a handle portion 71 with a longitudinal applicator portion 72 extending from each end of the handle portion. Each applicator portion 72 is offset laterally from the axis of handle portion 71 and may extend in the direction of said axis. Applicator portion 72 includes an end section 73 having a slightly convex receiving surface 74 against which is positioned a preshaped strip member 32 prior to application to an eyelid. The receiving surface 74 is treated with a coating of suitable release material so that strip member 32 may be readily separated from surface 74 when it is transferred to the skin surface of an eyelid. The end 75 of each end section 73 may be blunt to avoid injury to or aggravation of the eyelid skin during use of the applicator.

In the applicator device shown in FIGS. 16 and 17, the provision of two applicator portions 72 on opposite ends of handle portion 71 facilitates easy, quick application of strip members 32 to the right and left eyelids since the applicator device can be prepared with a strip member 32 on each applicator portion and the strip members may then be readily sequentially transferred to the two eyelids.

The applicator device 70 is readily used as generally indicated in FIG. 16. When one finger has lifted the loose eyelid skin 10, the applicator device carrying a strip member 32 on the end section thereof may be readily manipulated by the other hand to place the strip member 32 on the surface of the eyelid as previously described. The three dimensional curvature of the end section 73 facilitates placement of the strip member 32 on the three dimensional curvature of the eyelid. Such placement may be made by lowering the end section onto the eyelid so as to simultaneously press all areas of the strip member against the eyelid for adhesion thereto. In some eyelid configurations, it may be desired to place one end of strip member 32 on the eyelid surface adjacent the medial canthi and then progressively lay and lightly press the strip member on the remaining eyelid by rocking movement of the handle (or visa versa). When the strip member has been fully engaged with the skin surface of the eyelid, the adhesion to the eyelid is sufficiently strong to permit the applicator end section 73 to be detached from the strip member by lifting the end section off the strip member. The release coating on the receiving surface 74 facilitates this release. The redundant eyelid skin 10 may then be laid over the strip member as previously described.

In FIG. 18 a different modification of the applicator device is shown. In this example, handle portion 71' is elongated and straight. At one end, an applicator portion 72' is provided having an end section 73' of a configuration similar to that of end section 73. The end section 73' is provided with a receiving surface 74 having a suitable release coating thereon to permit ready detachment of a strip member 32 which may be applied thereto as described above with respect to applicator device 70. The length of handle portion 71' is selected to facilitate holding of the applicator device by a hand.

Optionally, the liner 48 can be pre-marked with curved strip patterns to be handcut out and/or modified, or be made with a surface for tracing patterns thereupon at time of use for cutting and/or modifying.

Thus, from the foregoing description, it can be seen that the method, adhesive strip member, and applicator of the present invention allows a non-surgical tuck to be taken in loose skin in general and, more particularly, in the upper eyelid to accomplish a temporary pseudo upper blepharoplasty.

It will be readily apparent that various modifications and changes may be made in the strip member 32 in the applicator devices 70 and 70' and in the method which falls within the spirit of this invention and all such changes and modifications coming within the scope of the appended claims are embraced thereby.

I claim:

1. A precut shaped, tape strip member for non-surgically taking a tuck in loose foldable skin of an upper eyelid with three dimensional skin surfaces in juxtaposed relation, such as in a tuck in an upper eyelid to effect a temporary pseudo upper blepharoplasty, comprising in combination:

a backing material which is thin, in the order of 1 to 3 mils., transparent, pliable, hypo-allergenic and adapted to conform to said skin surfaces, said backing material having side surfaces, a width of approximately 1 centimeter, a length approximately 5 centimeters, side edges curved over a major portion of their length to provide a convex side edge and an opposite concave side edge, and adapted to be positioned between the medial and lateral canthus and above the ciliary margin of an eyelid;

and an adhesive on both side surfaces adapted to releasably adhere to said opposed skin surfaces;

said backing material with said adhesive thereon being shaped to have adhesive areas of varying width throughout the length thereof to adapt said strip member to said juxtaposed three dimensional skin surfaces and to maintain a virtually unnoticeable line across the upper eyelid at the folded skin;

said strip member being concealable between the folded skin.

2. A strip member as stated in claim 1 wherein the shape of said member includes at least one longitudinal edge curved to correspond to the ciliary margin of an eyelid.

3. An adhesive concealable tape strip to effect a temporary pseudo upper blepharoplasty in which loose redundant folded eyelid skin is retained in folded unpressured relation to raise the ciliary margin of an upper eyelid relative to the eye, comprising:

a thin backing material which is hypo-allergenic, soft, pliable, strong, tear resistant, and of elongated tapered shape and precut to easily conform to skin surfaces of three dimensional configuration, said backing material being in the form of a short narrow elongated strip about 1 centimeter in width and about 5 centimeters in length; said narrow strip having side edges curved in the same direction for a major central portion of their length;

and a pressure sensitive adhesive lamina attached to each side of said backing material, said adhesive lamina adhering to said skin surfaces, and being water resistant, and non-irritating while also being releasable from skin surfaces with minimum irritation and difficulty.

4. A tape strip as stated in claim 3 wherein said backing is in the form of a short narrow elongated strip less than one centimeter in width and less than 5 centimeters in length.

5. An adhesive tape strip as stated in claim 3 wherein an edge of said backing material is curved to follow the line of the ciliary margin of an open eye, is about one centimeter in width at the widest point located adjacent the lateral canthus and tapers towards the medial canthus, and is about five centimeters in length.

6. An adhesive tape strip as stated in claim 3 wherein the adhesive on one side surface of said strip has adhering characteristics to skin greater than the adhesive substance on the opposite side surface of said strip.

* * * * *